United States Patent [19]

Abbas et al.

[11] Patent Number: 5,256,628
[45] Date of Patent: Oct. 26, 1993

[54] BIOLOGICAL CONTROL OF WEEDS USING AAL-TOXIN

[75] Inventors: Hamed K. Abbas, Greenville; Clyde D. Boyette, Leland, both of Miss.

[73] Assignee: The United States of America as represented by the Secretary of Agriculture, Washington, D.C.

[21] Appl. No.: 936,991

[22] Filed: Aug. 31, 1992

[51] Int. Cl.$^5$ .............................................. A01N 63/04
[52] U.S. Cl. .................................... 504/117; 504/117; 504/319; 504/353
[58] Field of Search ............. 71/79, 121, 120, DIG. 1; 504/117, 326

[56] References Cited

U.S. PATENT DOCUMENTS

| | | | |
|---|---|---|---|
| 4,419,120 | 12/1983 | Walker | 504/117 |
| 4,715,881 | 12/1987 | Anderson et al. | 504/117 |
| 4,929,270 | 5/1990 | Cardellina, II et al. | 71/92 |

OTHER PUBLICATIONS

Gilchrist, D. G., et al., "Production and Nature of a Host-Specific Toxin from *Alternaria alternate* f. sp. *lycopersici*", *Phytopathology*, Feb. 1976, vol. 66, pp. 165–171.
Bottini, A. T., et al., "Phytotoxins. I. A 1-Aminodimethylheptadecapenol from *Alternaria alternata* f. sp. *lycopersici*", *Tetrahedron Letters*, vol. 22 No. 29, pp. 2719–2722 (1981).
Bottini, At., et al., "Phytoxotins. II. Characterization of a Phytotoxic Fraction from *Alternaria alternata* f. sp. *lycopersici*", *Tetrahedron Letters*, vol. 22, No. 29, pp. 2723–2726 (1981).
Nishimura, S., et al., "Host-Specific Toxins and Chemical Structures from *Alternaria* Species," *Ann. Rev. Phytopathol.*, 1983, vol. 21, pp. 87–116.

*Primary Examiner*—Allen J. Robinson
*Assistant Examiner*—Deborah Lambkin
*Attorney, Agent, or Firm*—M. Howard Silverstein; John D. Fado; Joseph A. Lipovsky

[57] ABSTRACT

It has been discovered that AAL-toxin, a known host-specific phytotoxin produced by *Alternaria alternate* f. Sp. lycopersici, has a broad range as a pre-emergent or post-emergent bioherbicide. A method using AAL-toxin has been developed for controlling certain weeds, including duckweeds, jimsonweed, black nightshade, prickly sida, redroot pigweed and northern jointvetch. This phytotoxin can be used pure, as a cell-free filtrate, a crude filtrate, or a crude suspension of the culture.

6 Claims, No Drawings

BIOLOGICAL CONTROL OF WEEDS USING AAL-TOXIN

BACKGROUND OF THE INVENTION

1. Field of the Invention

The present invention relates to the biological control of several weed species by the use of a pathogenic toxin from a strain of the fungus *Alternaria alternate*.

2. Description of the Prior Art

Members of the genus Alternaria are known to produce a wide range of phytotoxic compounds which affect a large number of the plants on which the fungus is found (Bruce, V.R., Stack, M.E., and Mislivec, P.B. [1984] J. Food Sci. 49:1626-1627; Harvan, D.J., and Pero, R.W. [1976] J.V. Rodricks, ed. *Advances in Chemistry*, Series 149. pp 344-355). These phytotoxins include alternariol, alternariol monomethylether (AME), altenuene, altenuic acid, tenuazonic acid (TA), tentoxin, alternaric acid, AK-toxin, and AAL-toxin, and possess a broad range of biological activities and metabolic effects (Bruce et al., supra; Harvan et al., supra; Nishimura, S., and Kohmoto,K. [1983] Annual Rev. Phytopathology 21:87-116).

These phytotoxins have been referred to as 'host-specific' because they "are toxic only to the host that is susceptible to the pathogen which produces the toxin, and if they induce nearly all symptoms of the disease are considered to be definitive chemical probes in the study of disease susceptibility and physiological stress at the molecular level" (Bottinii A.T., and Gilchrist, D.G. [1981] Tetrahedron lett. 22:2719-2722). "Physiological, biochemical, genetic, and histological data all confirm that these toxic compounds are the key determinants of disease and of host selection by the producing fungi" (Scheffer, R.P. [1989] Kohmoto, K. and Durbin, R.D., ed. *Host-Specific Toxins*, pp. 1-17).

Furthermore, it is believed by phytopathologists that tolerance and sensitivity to a toxin is controlled by the same genes in the same way that they control resistance and susceptibility to the fungus (Scheffer, Robert P. and Livingston, Robert S. [1984] Science 223:17-21). If a fungus does not grow on a plant, the phytotoxin produced by the fungus will not affect that plant, depending on whether or not it has dominant or recessive alleles (Grogan, R.G., Kimble, K.A., and Misaghi, I. [1975] Phytopathology 65:880-886). In general, resistance in cultivare is equivalent to insensitivity to a metabolite released by the pathogen (Scheffer, R.P., supra). It has been suggested that these host-specific toxins are suitable for use as tools for screening resistant genotypes in plant breeding programs (Clouse, S.D., and Gilchrist, D.G. [1987] Phytophilogy 77:80-82; Clouse, S.D., Martensen, A.N. and Gilchrist, D.G. [1985] Journal of Chromatography 350:255-263; Scheffer et al., supra).

Even in a single species there may be a variety of strains which will be morphologically the same but can produce different toxins to which different hosts are susceptible. These are called pathotypes. *A. alternata* includes many pathotypes which are disease-producing in specific plants (Nishimura et al., supra; Stierle, A.C., Cardellina II, J.H., and Strobel, G.A. [1989] J. Natural Products 52:42-27).

One of these pathotypes is *A. alternate* f. sp. lycopersici which causes a serious stem canker disease affecting the leaves, stems, and fruits of susceptible tomato cultivars. However, the infection is unpredictable in that there are other tomato varieties which are unaffected by either the fungus or its toxin.

The structure of a host-specific phytotoxin responsible for stem canker disease has been elucidated. It was shown to be a long-chain ninhydrin-positive polyol called AAL-toxin (or Al-toxin) (Bottini, A.T., Bowen, J.R., and Gilchrist, D.G. [1981] Tetrahedron lett. 22:2723-2726; Bottini, A.T., and Gilchrist, D.G. supra). It has also been shown that in tomato cultivars which are susceptible to AAL-toxin, the pair of alleles involved is at the asc locus. The plants had three significantly different levels of toxin sensitivity, which were inherited as an incomplete dominant and corresponded to the genotype at the asc locus (Clouse et al. [1987] supra).

Apparently, however, not all stem canker disease is caused by AAL-toxin. A stem canker causing phytotoxin isolated from an *A. alternata* f. sp. lycoversici phytotype has been reported which did not react with ninhydrin indicating the absence of primary or aromatic amines. The toxin was effective on EarlyPak Tomatoes, but not on jimsonweed (*Datura stramonium*) or other solanaceous species tested (Gilchrist, D.G. and Grogan, R.G. [1975] Phytopathology 66:165-171).

There are many fungi which are pathogenic to weeds and which produce phytotoxins that could be useful as herbicides (Abbas, H.K., Boyette, C.D., Hoagland, R.E., and Vesonder, R.F., [1991] Weed Sci. 39:673-677;Boyette, C.D. [1986] Plant Sci. 45:223-228; Boyette, C.D., Weidemann, G.J., Te BeeBt, D.O. and Quimby, Jr., P.C., [1991] Weed Science 39:678-681); Stierle, et al., supra). Fusarium spp. are particularly plentiful throughout the world. An isolate of *Fusarium moniliforme*, obtained from infected jimsonweed, was found to produce fumonisin phytotoxin (Abbas, et al., supra). Fumonisin, while structurally similar to AAL-toxin, is obtained from a species known to have a broad host spectrum, whereas *A. alternata* f. sp. lycoversici is host-specific.

SUMMARY OF THE INVENTION

In view of the art described above, we were surprised to discover a method of controlling weeds of the type including duckweeds, jimsonweed, black nightshade, redroot pigweed, northern jointvetch, and prickly sida comprising applying to the weeds a phytotoxic amount of AAL-toxin produced by the fungus *A. alternata*. The AAL-toxin can be applied to the weeds in any suitable form including as cultures of the *A. alternata* fungus in water. Both a fungus-infected corn culture and a fungus-infested rice culture are likewise suitable. The AAL-toxin can be applied as a post-emergent or pre-emergent herbicide.

DETAILED DESCRIPTION OF THE INVENTION

*A. alternata* is easily isolated from susceptible tomato plants exhibiting symptoms of stem canker disease by known procedures (Abbas, H. K., supra). Isolates can be grown on potato-dextrose agar, malt agar and hay infusion agar and identified on the basis of conidial morphology (Ellis, M.B. [1971] *Dematiaceous Hyphomycetes* pp.464-466).

To produce AAL-toxin, the fungus is cultured on any suitable medium such as yellow corn kernels or converted long grain enriched rice (Abbas, H. K., supra). The AAL-toxin as identified is described below.

The bioherbicidal compositions of the invention are prepared by dispersing the cultures in suitable medium at application rate of active agent preferably ranging from about 0.1 to about 2.0 Kg/hectare. Suitable media include inert solid, powder, or granular, dry materials or liquid materials. Water is a particularly suitable material for dispersing AAL-toxin-containing cultures. The compositions can include non-inert material such as fertilizers, herbicides and the like. Suitable concentrations of the toxin can be determined easily by those skilled in the art as will become clear from the examples, but is preferably in the range of about 0.0001% to about 99.9% by weight. As a practical matter, it is suitable to use formulations of AAL-toxin from crude fungal inocula or fractions thereof, such as cell-free filtrates, thereby obviating the need to isolate the pure compound. However, formulations of the pure compound are certainly suitable.

The phytotoxic amount (i.e. that amount needed to kill the weed) of AAL-toxin in each formulation can be determined easily for each target weed species by anyone skilled in the art.

A preferred method of applying AAL-toxin containing formulations is by spraying pout-emergent weeds or by spraying soil before the weeds emerge. Other methods of application will be obvious to those skilled in the art.

The following examples are intended only to further illustrate that which the inventors believe to be their invention and should not be taken as limiting the present invention in any way.

Example 1

Nine *Alternaria alternata* and two *Cladosporium cladasporioides* isolates were obtained from infected 'Beefsteak' tomato plants exhibiting symptoms of stem canker disease. The isolates were grown on potato-dextrose agar (PDA), malt agar and hay infusion agar and stock cultures of these were maintained in the SWSL fungal repository on PDA and in the NRRL/ARS Culture Collection, Peoria, Ill. One *A. alternata* f. sp. lycopersici was provided by D.G. Gilchrist, Dept. of Plant Pathology, University of California, Davis, Calif., as *A. alternata* AS 27–32P. This isolate was used in these studies as a positive control because it is known to produce AAL-toxin, and is reported to cause stem canker in certain varieties of tomatoes. The isolates were given the designation of *A. alternata* SWSL 1, 2, 3, 5, 6, 8, 10, 11, and 12, *C. cladasporioides* SWSL 7 and 9, and *A. alternata* AS 27–32P was designated as SWSL 4.

Corn meal agar (CMA) cultures (12 to 14 days old) of isolates SWSL 1–12 were homogenized at 22° to 24° C. in 50 mL sterilized distilled water. This inoculum contained conidia and mycelium at a propagule density of $2 \times 10^7$ mL$^{-1}$.

A second inoculum was produced by growing the isolates on autoclaved, converted long-grain enriched rice. The fungus and rice were incubated for 28 days at 24° to 26° C. at 35 to 37% moisture content. The fungus-infested rice was transferred to screen-bottomed trays and allowed to air-dry at room temperature 22° to 26° C. for 72 to 96 hours in a ventilated hood. Two hundred grams of fungus infested rice were ground into a fine powder. Twenty grams of the fungus-infested rice powder were added to 100 mL of distilled water, stirred for 1 to 2 minutes, sonicated for 15 minutes and then sieved through double cheese cloth. The resulting preparation consisted of spores and mycelium at a propagule density ranging from 1 to $10^4$ mL$^{-1}$ as determined by hemacytometer counts.

Standard samples of alternariol, alternariol monomethyl ether (AME) and tenuazonic acid (TA) were obtained commercially. Tentoxin was provided by S.O. Duke [USDA-ARS, Southern Weed Science Laboratory (SWSL), Stoneville, Miss.]. AAL-toxin was purified from a crude filtrate of *A. alternata* f. sp. lycopersici grown on liquid media. Pure AAL-toxin was used at concentrations of 0.2 mg/ml distilled water; TA at concentrations of 25 mg/60 mL of 10% DMSO; and AME at concentrations of 20 mg/60 mL 10% DMSO.

Crude filtrates were prepared by homogenizing 40 g of fungus-infested rice in 200 mL distilled water and filtering through a double layer of cheese cloth. Half of this filtrate was taken to produce cell-free filtrate by filtration through 0.45 μm Millipore filters. For the phytotoxin test, 100 g of fungus-infested rice were extracted successively with hexane (300 mi), dichloromethane (2x, 300 mL) and 60% (v/v) aqueous methanol (300 mL). AME was detected in the dichloromethane extract by thin layer chromatography (TLC) on silica-gel plates (E.Merck, Darmstadt, West Germany) developed in the solvent system chloroform:methanol [95:5 (v/v)] versus AME standards. AME was isolated by silica-gel column chromatography at a concentration of 58 mg per 100 g of fungus-infested rice. Identity of AME was confirmed by comparison of its NMR, UV, and IR spectra with authentic samples. TA and AAL-toxin were detected on $C_{18}$ reverse phase TLC plates in the solvent system methanol:water [75:25 (v/v)] versus authentic samples. These two toxins were isolated by $C_{18}$ reverse phase chromatography using methanol:water [65:35 (v/v)]. Their identities were confirmed by co-chromatographing each metabolite with authentic samples. TA was further characterized by its IR and UV spectra. The fungus-infested rice extracts of isolates containing AME, TA and AAL-toxin were analyzed for tentoxin and alternariol. Neither one was detected.

Only the extracts of SWSL 1 were found to contain the following phytotoxins at the indicated concentrations: AAL-toxin (100 μg/g rice media); tenuazonic acid (TA) [10, μg/g]; and alternariol monomethyl ether (AME) [580 μg/g] (Table 1). Tentoxin and alternariol were not detected in the fungus-infested rice extracts of any of these isolates. The extract of SWSL 4 was found to contain the phytotoxin AAL-toxin at a rate of 85, μg per g of fungus infested rice.

TABLE 1

Production of Phytotoxin by *Alternaria alternata* grown on rice.

| Phytotoxin | Concentration μg for g fungus-infected rice |
| --- | --- |
| AAL-toxin | 100 |
| Tenuazonic acid (TA) | 10 |
| Alternariol monomethyl ether (AME) | 580 |
| Alternariol | ND |
| Tentoxin | ND |

Pathogenicity tests on jimsonweed: Jimsonweed seeds were mechanically scarified with sandpaper and planted in a commercial potting mixture supplemented with a slow release fertilizer (N:P:K 14:14:14), contained in peat strips ($12 \times 5.5$ cm$^2$ pots/strip). The plants were watered as needed, and the greenhouse temperature was maintained between 28° and 32° C. with 40 to 60% relative humidity. The photoperiod was ca. 14 h at ca. 1600 to 1899 uE.m.$^{-2}$s$^{-1}$ at midday. The fungal inoculum from each isolate was applied with an atomizer to run-off. Control groups received a filtrate of autoclaved rice or distilled water. Jimsonweed plants, 1 and 2 wks old (2- to 4 leaf stage) were used in these experiments. Following inoculation, plants were incubated on greenhouse benches under conditions as described above. Three replicates of 12 plants each were used for each treatment. The experiment was repeated twice. Symptom development was monitored daily. Heights of six Jimsonweed plants were measured at the beginning and the end of the experiments. Dry weights of plant material above the soil were determined at the end of the experiments after drying for 48 hr at 60° to 70° C. The results are shown in Table 2.

In intact plants, the damage resulting from the crude, cell-free filtrates and the AAL-toxin was identical, including various sizes of necrotic spots on the leaves and stems of intact plants. The growth and dry weight of plant material biomass were affected similarly by the cell-free filtrate, AAL-toxin and crude filtrate. The reduction in biomass was 68% and 46% for AAL-toxin and cell-free filtrate, respectively. Plant height was reduced by cell-free filtrates and AAL-toxin significantly, as compared to control groups. DMSO (10% v/v) incited identical damage as AME and TA in DMSO. This indicates that DMSO was responsible for the damage to the leaves of intact plants. The two *C. cladasporioides* isolates (SWSL 7 and SWSL 9) from the same infected tomato plants were neither pathogenic nor did they produce any detectable phytotoxins. They were therefore used as controls for the method.

The crude filtrates of isolates SWSL 4 and SWSL 1 each contained AAL-toxin which caused similar damage to jimsonweed plants.

SWSL 1 was deposited in the NRRL/ARS Culture Collection, Peoria, Ill. and was designated as NRRL#18822.

TABLE 2

Effects of various *Alternaria alternata* isolates and various phytotoxins on the growth of 2-wk old jimsonweed.

| Fungus or Phytotoxins (Source) | Code no. | Absolute amt. of toxins used (mg) | Plant Height[a] change (cm) | Dry Weight[b] reduction (%) |
|---|---|---|---|---|
| *Alternaria alternata* (Tomato plants) | SWSL 1 | 2 (AAL) | 11.6 | 31 |
| | 2 | ND | 16.7 | 12 |
| | 3 | ND | 18.3 | 5 |
| | 5 | ND | 16.3 | 12 |
| | 6 | ND | 16.3 | 1 |
| | 8 | ND | 16.9 | 1 |
| | 10 | ND | 18.3 | 9 |
| | 11 | ND | 18.3 | 5 |
| | 12 | ND | 18.3 | 1 |
| *Alternaria alternata* (AS 27-32P) (Pure culture) | SWSL 4 | 1.6 (AAL) | 12.0 | 27 |
| *Cladosporium cladasporioides* (Tomato plants) | SWSL 7 | ND | 17.0 | 1 |
| | 9 | ND | 17.0 | 1 |
| Control | H$_2$O | — | 17.4 | 1 |
| Crude-filtrate (Rice-infested fungus) | SWSL 1 | 2 (AAL) | 8.7 | 44 |
| Cell-free filtrate (Rice-infested fungus) | SWSL 1 | 1.8 (AAL) | 9.9 | 46 |

TABLE 2-continued

Effects of various *Alternaria alternata* isolates and various phytotoxins on the growth of 2-wk old jimsonweed.

| Fungus or Phytotoxins (Source) | Code no. | Absolute amt. of toxins used (mg) | Plant Height[a] change (cm) | Dry Weight[b] reduction (%) |
|---|---|---|---|---|
| AAL-toxin | SWSL 1 | 4 | 3.4 | 68 |
| Tenuazonic acid | TA | 25 | 8.1 | 45 |
| Alternariol monomethyl ether | AME | 20 | 7.6 | 45 |
| Dimethyl sulfoxide | DMSO | 60 mL | 7.0 | 43 |
| Controls | H$_2$O | 60 mL | 16.4 | 2 |

[a]Means of six plants +/− standard deviation
[b]The mean of 3 replicates (each of 12 plants)
+/− standard deviation
ND = not detected Spores from either isolate grown on CMA applied to jimsonweed at a rate of 2×10$^7$ spores/ml, with or without dew period did not produce any symptoms.

Example 2

Excised jimsonweed leaves were used to test the biological activities of crude and cell-free filtrates and secondary metabolites. Excised leaves were placed on moistened filter paper inside 9-cm diameter sterile petri plates. The inocula of crude filtrates, cell-free filtrates, and the phytotoxin standards were applied to the leaves with micropipets. Amounts used were 100 μl to adaxial or abaxial surfaces at concentrations of: (a) 20 g/100 mL distilled water for the crude and cell-free filtrates; (b) 25 mg of TA dissolved in 60 mL of 10% DMSO; (c) 35 mg of AME dissolved in 60 mL of 10% DMSO; and (d) AAL-toxin 0.2 mg mL$^{-1}$ distilled water. Six leaves were used for each treatment. Control leaves received either rice filtrate, distilled water, or 10% (v/v) DMSO. The plates were sealed with parafilm and incubated under continuous or 12 h light (20 uE.m.$^{-2}$s$^{-1}$). The phytotoxic effects on the treated excised leaves were evaluated visually for damage for 14 days. Crude and cell-free filtrates and AAL-toxin caused similar damage to excised leaves, characterized by autolysis diffusing from the point of treatment along the veins adaxially or abaxially to leaves. AME and TA caused no visible damage to excised leaves after 10 days, while the 10% DMSO solution caused moderate-to-severe necrosis. After 12 days, TA-treated plants exhibited chlorotic halos around the treatment points. These phytotoxins all required high concentrations (>1000 μg/mL) to be effective. Results are shown in Table 3.

TABLE 3

Effects of fungal filtrates and secondary metabolites produced by *A. alternata* on excised leaves of jimsonweed.*

| Fungal filtrates or toxins | Code No. | Conc. (μg/mL) | Amt./Material (mg) leaf | Phytotoxicity |
|---|---|---|---|---|
| Control | H$_2$O | 100% | 0.10 mL. | — |
| Crude-filtrate (Rice-infested fungus) | SWSL #1 | 200 | 2.00 | + |
| Cell-free filtrate (Rice-infested fungus) | SWSL #1 | 200 | 2.00 | + |
| AAL-toxin | SWSL #1 | 0.2 | 0.02 | + |
| Tenuazonic acid** | TA | 0.42 | 0.04 | + |
| Alternariol | AME | 0.58 | 0.06 | + |

TABLE 3-continued

Effects of fungal filtrates and secondary metabolites produced by *A. alternata* on excised leaves of jimsonweed.*

| Fungal filtrates or toxins | Code No. | Conc. (μg/mL) | Amt./Material (mg) leaf | Phyto-toxicity |
|---|---|---|---|---|
| monomethyl ether Dimethyl-sulfoxide | DMSO | 10% | 0.10 mL | — |

*Six leaves were used for each treatment. The phytotoxic damages were evaluated visually for 14 days.
— = no phytotoxic effects
+ = phytotoxic effects
**Leaves showed chlorotic halos around the treatment points after 12 days.

Example 3

AAL-toxin was applied to excised jimsonweed and black nightshade (*Solanum nigrum* L.) true leaves to determine a dose-response curve. Primary and secondary leaves from greenhouse-grown 20-day-old jimsonweed plants were used in this study. The primary and secondary leaves were obtained from 20-day-old black nightshade plants (seeds were purchased from Thompson Seed Co., Fresno, Calif.). The AAL-toxin used in this study was produced and purified in the following manner.

A. Growth of cultures:

Two hundred grams of Uncle Ben's converted long-grain enriched parboiled rice (Uncle Ben's, Inc., Houston, Tex.) were placed with 120 mL of distilled water into one liter flasks and were allowed to stand about one hour until the water was absorbed. The flasks were shaken to uniformly distribute the moist substrates, closed with tight cotton stoppers and autoclaved 60 min at 15 lbs pressure. Immediately after autoclaving, the flasks were shaken vigorously to break up clumps. They were allowed to stand 24 hr and the autoclaving and shaking process was repeated. The flasks were then inoculated as soon as they were cool, using isolates of *Alternaria alternata* NRRL 18822, and maintained in stock cultures on corn meal agar slants in small vials. To recover the fungus, a small piece of inoculum was placed on PDA for 7 to 10 days. One to two cm² inoculum was removed and added to autoclaved rice. The flasks were incubated in the incubator at 28° C. for 4 wks with daily shaking for the first few days to permit the fungus to penetrate the rice uniformly. Shaking was discontinued after complete invasion approximately 5–7 days after inoculation. The fungus and rice were stored for 4 wks in the incubator 12 h light and 12 h dark. The fungus-infested rice was transferred to a screen-bottomed tray, was allowed to air dry in a ventilated hood, was ground to the consistency of flour, and used on these studies (biological and chemical).

B. Extraction:

One kg of fungus-infested rice was soaked in chloroform overnight at a ratio of 1 gram fungus-infested rice: 5 mL of chloroform. This was placed in a blender for 5 min at high speed. The chloroform layers were discarded. The residue which contained AAL-toxin was transferred to a screenbottomed tray and was allowed to air dry in a ventilated hood. The dried residue was soaked in H₂O:methanol (60:40) overnight, at a ratio of 1 gram fungus-infested rice per 5 mL of extracting solvent. This was placed in a blender for 5 min at high speed. The filtrate was collected by centrifugation. The extracting process was repeated 2 times with residue as described above. The filtrates were combined and the methanol was removed by rotary evaporator. The AAL-toxin is in the water layers.

C. Purification:

This process was patterned after fumonisin purification as described in detail by Vesonder, R.F., R.E. Peterson, R.D. Plattner, and D. Weisleder. [1990] Mycotoxin Res. 6:85–88. Briefly, the water aliquot was passed through an Amberlite XAD-2 (Sigma Chemical Co.) column. The Amberlite XAD-2 column was washed successively with distilled water and methanol. The methanol eluate contained AAL-toxin as evidenced on TLC $c_{18}$ reverse-phase plate with $F_{254s}$ fluorescent indicator (EM Science, Cherry Hill, N.J.) versus an authentic sample developed in the solvent system methanol:water (75:25). The AAL-toxin contained in the methanol eluate was purified by flash column chromatography on a 50 gram reverse-phase $C_{18}$ packing (Water Associates, Milford, Mass.). The column was eluted with 60% aqueous methanol, and 10 mL fractions collected. A white solid was obtained in the fractions containing AAL-toxin. Twenty milligrams of 95% pure AAL-toxin was obtained from 430 mg of crude toxin contained in the methanol eluate from the XAD-2 column. The AAL-toxin identity was confirmed by FAB-mass spectrometry (M+peak at 522).

AAL-toxin (14.2 mg) was dissolved in 71 mL sterile distilled water to yield a 200 μg/ml solution. This stock solution was diluted serially by two with equal amounts distilled water to a concentration of 0.01 μg/ml (10 ng/mL).

Six leaves were used for each treatment. Control leaves received distilled water. Excised leaves were placed on moistened filter paper inside 9-cm sterile Petri plates. The different concentrations of AAL-toxins were applied to the leaves with a 10 μl micropipette, 4 to 12 times per leaf, depending on its size. The absolute amount of each application was determined. The plates were incubated under 14 h light (498 $\mu E.m.^{-2}s^{-1}$) in the growth chamber at 25° C. with 80–85% R.H. Observations of phytotoxicity were made at frequent intervals for five days. The results are shown in Table 4.

TABLE 4

Effects of AAL-toxin on jimsonweed and black nightshade leaves.

| Toxin concentration (μg/mL) | Absolute amt. of toxin/drop (ng) | Phytotoxicity | |
|---|---|---|---|
| | | Jimson-weed | Black nightshade |
| 0 | 0 | — | — |
| 0.01 | 0.1 | — | + |
| 0.02 | 0.2 | — | + |
| 0.05 | 0.5 | — | + |
| 0.10 | 1 | — | + |
| 0.20 | 2 | — | ++ |
| 0.39 | 3.9 | — | ++ |
| 0.78 | 7.8 | — | ++ |
| 1.56 | 15.6 | + | +++ |
| 3.13 | 31.3 | + | +++ |
| 6.25 | 62.5 | + | +++ |
| 12.5 | 125 | ++ | +++ |
| 25 | 250 | ++ | +++ |
| 50 | 500 | +++ | +++ |
| 100 | 1000 | +++ | +++ |
| 200 | 2000 | +++ | +++ |

Six leaves were used for each treatment. Control groups received distilled water. Leaves were incubated under 14 hours light (498 $\mu E.^{-1}m.^{-2}s.^{-1}$) in growth chamber at 25° C. for five days. Absolute amount of AAL-toxin per drop (each 10 μL) was calculated based on volume and concentration of the pure toxin.
— = No phytotoxicity observed
+ = Less than ⅓ of leaf autolyzed
++ = Less than ½ of leaf autolyzed
+++ = More than ½ of leaf autolyzed

Example 4

Thirty-one weed and cultivated plants from 10 families were used. They ranged in age from seven to ten days old at the time of spraying. Seeds of plants used in these experiments were obtained from commercial companies or collected locally. The number of plants of each cultivar varied between ten to fifty per pot depending on the plant species. Seeds of each cultivar were planted in a vermiculite potting mixture as described previously. The experiment was confirmed by repeating twice. One concentration of AAL-toxin at 0.2 mg/ml was prepared in 50 mL distilled water. Filtrate of fungus-infested rice was prepared by homogenizing 20 g in 100 mL distilled water and filtering through a double layer of cheese cloth. An aerosol sprayer was used to spray the AAL-toxin solutions and *A. alternata* filtrates on the plants until run off. Plants were kept in the greenhouse under the same conditions as described in Example 1. Symptoms were observed daily until the end (last two weeks) of the experiment and included chlorosis, necrosis, stunting and mortality. The results are shown in Table 5.

TABLE 5

Response of various crop and weed species tested for susceptibility to AAL-toxin and *Alternaria alternata* NRRL 18822.

| FAMILY<br>Common name, scientific name, cultivar | Disease reaction[a] |
|---|---|
| AMARANTHACEAE | |
| Redroot pigweed, (*Amaranthus retroflexus* L.) | S-5 |
| COMPOSITAE | |
| Cocklebur (*Xanthium strumarium* L.) | S-2 |
| CONVOLVULAVEAE | |
| Morningglory (*Ipomoea wrightii* Gray) | I |
| CUCURBITACEAE | |
| Cucumber (*Cucumis sativus* L.) | S-2 |
| GERANIACAEA | |
| Wild geranium (*Geranium dissectum* L.) 'cutleaf' | S-3 |
| 'Carolina' | S-2 |
| GRAMINEAE | |
| Barley (*Hordeum vulgare* L.) | I |
| Bermuda grass [*Cynodon dactylon* (L.) pers.] | I |
| Corn (*Zea mays* L.) 'Truckers Favorite' | I |
| Johnsongrass [*Sorghum halepense* (L.) Pers.] | S-1 |
| Oats (*Avena sativa* L.) | I |
| Rice (*Oryza sativa* L.) | S-1 |
| Grain sorghum [*Sorghum bicolor* (l.) Moench] 'Texas C-124' | I |
| Wheat (*Triticum aestivum* L.) | I |
| LEGUMINOSAE | |
| Alfalfa (*Medicago sativa* L.) | S-3 |
| Crimson clover (*Trifolium incarnatum* L.) | S-3 |
| Sicklepod (*Cassia obtusifolia* L.) | S-2 |
| Hemp sesbania (*Sesbania exalta* (Raf.) Cory.) | S-4 |
| Northern jointvetch [*Aeschynomene virginica* (L.) B.S.P.] | S-5 |
| American jointvetch (*Aeschynomene americna* L.) | S-1 |
| Indian jointvetch (*Aeschynomene indica* L.) | S-2 |
| Soybean [*Glycine max* (L.) Merr.] | |
| 'Forrest' | S-1 |
| 'Centennial' | S-1 |
| LEMNACAEA | |
| Common duckweed (*Lemna minor* L.) | S-5 |
| Duckweed (*Lemna pausicostata* L.) | S-5 |
| MALVACEAE | |
| Cotton (*Gossypium hirsutum* L.) 'Stoneville 213' | S-1 |
| Prickly sida (*Sida spinosa* L.) | S-5 |
| Velvetleaf (*Abutilon theophrasti* Medic.) | S-1 |
| Spurred anoda [*Anoda cristata* (L.) Schlect) | S-2 |
| SOLANACAEA | |
| Tomato (*Lycopersicon esculentum* Mill) | |
| 'Beefsteak' | S-2 |
| 'Marion' | S-2 |
| Jimsonweed (*Datura stramonium* L.) | S-5 |

[a]Reaction:
S = susceptible, where 1 equals small (1 mm), non-enlarging lesions to 5 equals plant death;
I = immune.

We claim:

1. A method of controlling weeds of the group consisting of duckweeds, jimsonweed, redroot pigweed, northern jointvetch, prickly sida, and black nightshade comprising applying to said weeds a phytotoxic amount of AAL-toxin.

2. The method of claim 1 wherein said AAL-toxin is applied to said weeds as a culture of AAL-toxin-producing fungus *Alternaria alternata* in water.

3. The method of claim 1 wherein said AAL-toxin is applied by spraying.

4. The method of claim 1 wherein the fungus is *Alternaria alternata*, NRRL #18822.

5. The method of claim 2 wherein said culture is a corn meal agar culture.

6. The method of claim 2 wherein said culture is a fungus-infested rice powder culture.

* * * * *

UNITED STATES PATENT AND TRADEMARK OFFICE
CERTIFICATE OF CORRECTION

PATENT NO. : 5,256,628
DATED : October 26, 1993
INVENTOR(S) : Hamed K. Abbas; Clyde D. Boyette; Ronald F. Vesonder It is certified that error appears in the above—identified patent and that said Letters Patent is hereby corrected as shown below:

On the Title page, Item [75] should read:

Inventors: Hamed K. Abbas, Greenville; Clyde D. Boyette, Leland, both of Miss.; Ronald F. Vesonder, Peoria, Il.

Signed and Sealed this

Tenth Day of May, 1994

Attest:

BRUCE LEHMAN

Attesting Officer         Commissioner of Patents and Trademarks